United States Patent [19]

Bowman et al.

[11] Patent Number: 5,011,999
[45] Date of Patent: Apr. 30, 1991

[54] PROCESS OF PREPARING NON-CYCLIC POLYALKYLENEPOLYAMINES EMPLOYING GROUP VB METAL CATALYSTS

[75] Inventors: Robert G. Bowman; George E. Hartwell; David C. Molzahn, all of Midland, Mich.; Enrique G. Ramirez; John E. Lastovica, Jr., both of Lake Jackson, Tex.

[73] Assignee: The Dow Chemical Company, Midland, Mich.

[21] Appl. No.: 314,528

[22] Filed: Feb. 23, 1989

[51] Int. Cl.$^5$ .............. C07C 209/16; C07C 209/64; C07D 295/023; C07D 295/13

[52] U.S. Cl. .................... 564/479; 544/352; 544/358; 544/401; 544/402; 564/305; 564/346; 564/355; 564/360; 564/367; 564/368; 564/371; 564/372; 564/402; 564/443; 564/470; 564/474

[58] Field of Search .............. 564/479, 305, 346, 355, 564/360, 367, 368, 371, 372, 402, 443, 470, 474; 544/358, 352, 401, 402

[56] References Cited

U.S. PATENT DOCUMENTS

| 2,073,671 | 5/1937 | Andrews | 260/127 |
|---|---|---|---|
| 2,113,241 | 4/1938 | Punnett | 260/127 |
| 2,456,599 | 12/1948 | Smith | 260/585 |
| 3,231,616 | 1/1966 | Jones | 260/581 |
| 3,270,059 | 8/1966 | Winderl et al. | 260/583 |
| 3,387,032 | 6/1968 | Leonard | 260/585 |
| 3,714,259 | 1/1973 | Lichtenwalter et al. | 260/583 P |
| 4,036,881 | 7/1977 | Brennan et al. | 260/583 P |
| 4,044,053 | 8/1977 | Brennan et al. | 260/583 P |
| 4,103,087 | 7/1978 | Brennan | 544/78 |
| 4,217,240 | 8/1980 | Bergna | 252/313 S |
| 4,324,917 | 4/1982 | McConnell | 564/479 |
| 4,376,732 | 3/1983 | Ramirez | 260/239 E |
| 4,394,524 | 7/1983 | Ford et al. | 564/479 |
| 4,448,997 | 5/1984 | Brennan et al. | 564/479 |
| 4,463,193 | 7/1984 | Johnson et al. | 564/479 |
| 4,495,369 | 1/1985 | Werner et al. | 564/480 |
| 4,540,822 | 9/1985 | Vanderpool | 564/479 |
| 4,550,209 | 10/1985 | Unvert et al. | 564/479 |
| 4,552,961 | 11/1985 | Herdle | 544/402 |
| 4,560,798 | 12/1985 | Ford et al. | 564/503 |
| 4,578,517 | 3/1986 | Johnson et al. | 564/479 |
| 4,578,518 | 3/1986 | Vanderpool et al. | 564/479 |
| 4,578,519 | 3/1986 | Larken et al. | 564/479 |
| 4,582,904 | 4/1986 | Wells et al. | 544/178 |
| 4,584,406 | 4/1986 | Vanderpool et al. | 564/479 |
| 4,588,842 | 5/1986 | Vanderpool | 564/479 |
| 4,609,761 | 9/1986 | Watts, Jr. et al. | 564/479 |
| 4,612,397 | 9/1986 | Renken | 564/479 |
| 4,613,705 | 9/1986 | Hargis | 564/409 |
| 4,617,418 | 10/1986 | Ford et al. | 564/479 |
| 4,683,335 | 7/1987 | Knifton et al. | 564/480 |
| 4,906,782 | 7/1990 | Hara et al. | 564/478 |

FOREIGN PATENT DOCUMENTS

| 0256516 | 2/1988 | European Pat. Off. |
| 48-96475 | 12/1973 | Japan |
| 8335179 | 3/1983 | Japan |
| 1183249 | 8/1986 | Japan |
| 2147896 | 5/1985 | United Kingdom |

OTHER PUBLICATIONS

Derwent 89-235462/33.
Derwent 89-232291/32.
Derwent 89-225659/31.
Derwent 89-223168/31.
Derwent 89-216477/30.
Derwent 89-195638/27.
Derwent 89-132555/18.
Derwent 89-139204/19.
Derwent 55652C/32 (1980).
Derwent 85-044573/08 (1985).
Chemical Abstracts 99:38020p (1983).
Chemical Abstracts 103:70937e (1985).

Primary Examiner—Richard L. Raymond
Assistant Examiner—P. O'Sullivan

[57] ABSTRACT

A process for the preparation of predominantly non-cyclic polyalkylenepolyamines comprising contacting a difunctional aliphatic alcohol with ammonia or a primary or secondary aliphatic amine in the presence of a catalyst selected from the group consisting of Group VB metal oxides, niobium phosphates, tantalum phosphates, and mixtures thereof. For example, monoethanolamine is aminated by ethylenediamine to predominantly linear and branched polyethylenepolyamines in the presence of a catalyst containing niobium oxide supported on boehmite alumina.

26 Claims, No Drawings

PROCESS OF PREPARING NON-CYCLIC POLYALKYLENEPOLYAMINES EMPLOYING GROUP VB METAL CATALYSTS

Background of the Invention

This invention relates to a process for preparing non-cyclic polyalkylenepolyamines, such as diethylenetriamine, and linear and branched triethylenetetramines.

Non-cyclic polyalkylenepolyamines find utility as dispersants, surfactants, chelants, catalysts, curing agents, extenders in polyurethanes, and as starting materials in the preparation of pesticides.

It is known that non-cyclic polyalkylenepolyamines can be prepared by the reaction of an alkyl halide with ammonia or an amine. The product is a polyalkylenepolyamine hydrohalide salt, which must be neutralized with base in order to recover the valuable polyalkylenepolyamine product. The neutralization produces a waste stream of metal salt, which must be removed. Moreover, the process produces a considerable amount of cyclic compounds.

It is known that salt-free non-cyclic polyethylenepolyamines can be directly prepared by reacting an ethyleneamine with an ethanolamine in the presence of hydrogen and a hydrogenation catalyst. For example, U.S. Pat. No. 3,714,259 discloses such a process with preferred catalysts derived from the oxides of chromium, copper, nickel, and cobalt. The process produces only the lower polyethylenepolyamines, and substantial quantities of piperazine.

More recently it is known to prepare non-cyclic polyalkylenepolyamines directly by reacting an alkanolamine with an alkyleneamine under non-reductive conditions, that is, in the absence of hydrogen. Many of the non-reductive aminations are known to employ a phosphorous containing catalyst. U.S. Pat. No. 4,036,881, for example, teaches the use of acidic metal phosphates, phosphoric acid compounds, and organic phosphates in the reaction of an alkanolamine with an alkyleneamine. U.S. Pat. No. 4,448,997 teaches a similar process except that an aluminum phosphate catalyst prepared from alumina and phosphoric acid is employed. These phosphorus-containing catalysts are soluble in amines. Consequently, the catalysts leach into the reaction causing catalyst losses and separation problems.

Other non-reductive processes are known employing phosphorus-containing catalysts. U.S. Pat. No. 4,463,193, for example, discloses the production of non-cyclic polyalkylenepolyamines by reacting an alkanolamine with an alkyleneamine and ammonia in the presence of a Group IIIB metal acid phosphate, including the rare earth lanthanide metals. U.S. Pat. No. 4,578,518 is representative of a series of patents drawn to the production of linear polyethylenepolyamines from ethylenediamine and monoethanolamine using catalysts comprising titania having phosphorus deposited thereon. These phosphorus-containing catalysts lose their physical integrity in the presence of water, which is a by-product of the amination reaction. Moreover, these catalysts can react with water to release free phosphoric acid or amine phosphate salts. Consequently, these catalysts can lose their phosphorus component and leach into the reaction mixture causing catalyst losses and separation problems.

U.K. Patent 2,147,896B discloses a process for producing diethylenetriamine by reacting monoethanolamine with ammonia in the presence of ethylenediamine and a Group VB metal phosphate. The mole ratio of phosphorus to Group VB metal is disclosed to be 1 for vanadium, and 1.5 and 3 for niobium and tantalum. Disadvantageously, these catalysts decompose in the reaction mixture, thereby shortening the catalyst lifetime and causing problems similar to those mentioned hereinbefore.

It would be advantageous to have a non-reductive amination process which produces non-cyclic polyalkylenepolyamines. It would be more advantageous if the catalyst for such a process is insoluble in the liquid reactant amines. It would be most advantageous if the catalyst for such a process retains its physical integrity in the presence of water. Such a process would eliminate the need for neutralizing hydrohalide salts and disposing of a waste salt stream. Such a process would also eliminate problems with catalyst leaching, reactor plugging, and catalyst separation. Accordingly, such an amination process would be suitable for industrial purposes

SUMMARY OF THE INVENTION

This invention is a process for preparing non-cyclic polyalkylenepolyamines which comprises contacting a difunctional aliphatic alcohol with a reactant amine in the presence of a catalyst containing a Group VB metal compound. The Group VB metal compound is selected from the group consisting of (a) Group VB metal oxides, (b) niobium phosphates and tantalum phosphates wherein the mole ratio of phosphorus to niobium or tantalum metal is no greater than about 1.3, and (c) mixtures thereof. The contacting of the difunctional aliphatic alcohol and the reactant amine with the catalyst is conducted under reaction conditions such that a mixture of polyalkylenepolyamines enriched in non-cyclic products is produced. For the purposes of this invention "non-cyclic products" are defined as amine products arising from condensation of the difunctional aliphatic alcohol and amine reactants. Non-cyclic products include linear and branched homologues. Non-cyclic products are to be distinguished from cyclic products, which arise from condensation of the alcohol and amine reactants followed by internal cyclization to form a nitrogen-containing heterocycle.

Advantageously, the process of this invention is capable of achieving higher yields of the valuable non-cyclic polyalkylenepolyamines, and lower yields of undesirable cyclic products. More advantageously, the process of this invention does not produce a waste stream of metal salts. Even more advantageously, the catalysts of this invention are insoluble in liquid amines; therefore, catalyst losses are minimized and separation of the polyamine products from the catalyst is relatively easy. Most advantageously the catalysts of this invention retain their physical integrity in the presence of water. Consequently, the catalysts possess a long lifetime and are suitable for industrial use.

The non-cyclic polyalkylenepolyamine products of this invention are useful as dispersants, surfactants, chelants, curing agents, and catalysts, and also useful in the formation of ureas, urethane polymers, and pesticides.

DETAILED DESCRIPTION OF THE INVENTION

The difunctional aliphatic alcohol which is employed in the process of this invention includes any aliphatic alcohol containing (a) at least one hydroxyl moiety bound to a primary carbon atom, and (b) at least one additional moiety selected from the group consisting of hydroxyl, primary amine or secondary amine functionalities. Examples of suitable difunctional aliphatic alcohols include diols such as ethylene glycol and propylene glycol, triols such as glycerol, and higher polyols; polyether polyols such as diethylene glycol, ethylene oxide capped polypropylene glycols, and higher homologues; alkanolamines such as monoethanolamine and N-(2-aminoethyl)ethanolamine; and polyether amino alcohols such as 2-($\beta$-aminoethoxy)-ethanol. The difunctional alcohols are not limited to the aforementioned examples, and other equally suitable difunctional alcohols can be employed in the practice of this invention.

Preferably, the difunctional alcohols are represented by the general formula:

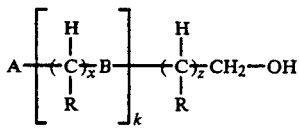

wherein A is OH or NHR; each B is independently NR or O; each R is independently hydrogen, hydroxyl, amino ($NH_2$), an alkyl moiety of $C_1$-$C_{12}$ carbon atoms such as methyl, ethyl or propyl, a hydroxyalkyl or aminoalkyl moiety of $C_1$-$C_{12}$ carbon atoms, or a monocyclic aromatic moiety, such as phenyl, or tolyl; x is a positive integer from 2 to about 12; k is a positive integer from 0 to about 150; and z is a positive integer from 0 to about 12. Preferably, each R is hydrogen. More preferably, each R is hydrogen, x is 2, and z is 1. Most preferably, each R is hydrogen, A is $NH_2$, k is 0, z is 1, and the difunctional aliphatic alcohol is monoethanolamine.

The reactant amines which are employed in the process of this invention include ammonia and any primary or secondary aliphatic amine which is capable of aminating the difunctional aliphatic alcohol. Examples of suitable reactant amines include aliphatic monoamines such as ethylamine, propylamine, n-butylamine, hexylamine, octylamine, diethylamine, dibutylamine, dihexylamine, dicyclohexylamine, dioctylamine, methylethylamine, and ethylpropylamine; linear and branched alkylene diamines and polyamines such as ethylenediamine, propylenediamine, diethylenetriamine, triethylenetetramines, and tetraethylenepentamines; alkylene ether polyamines such as 2-($\beta$-aminoethoxy)ethylamine; and mixtures of the above-identified amines. While the aforementioned amines are representative of those which are suitable for the process of this invention, other amines not recited herein may be equivalent and equally suitable.

Simple primary and secondary reactant amines which are preferred for the process of this invention are represented by the general formula $R^1_2NH$, wherein each $R^1$ is independently hydrogen or a $C_1$-$C_{12}$ alkyl moiety. Preferably, the reactant alkylenepolyamines and alkylene ether polyamines which are suitable in the process of this invention are represented by the general formula:

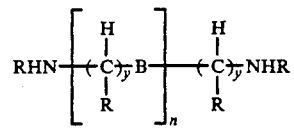

wherein each B is independently NR or O; each R is independently hydrogen, hydroxyl, amino, an alkyl moiety of $C_1$-$C_{12}$ carbon atoms such as methyl, ethyl, or propyl, a hydroxyalkyl or aminoalkyl moiety of $C_1$-$C_{12}$ carbon atoms, or a monocyclic aromatic moiety, such as phenyl or tolyl; each y is independently a positive integer from 2 to about 12, and n is a positive integer from 0 to about 150. Preferably, each B is NR and the amine is an alkylenepolyamine. More preferably, the amine is an alkylenepolyamine and each R is hydrogen. Even more preferably, each B is NR, each R is hydrogen, each y is 2, and the amine is an ethylenepolyamine. Most preferably, the reactant amine is ethylenediamine.

In accordance with the process of this invention, any mole ratio of reactant amine to difunctional aliphatic alcohol which enables the amination reaction to proceed to the desired non-cyclic polyalkylenepolyamine products is suitable. Typically, the alcohol is reacted with at least about one mole equivalent of reactant amine; however, an excess of reactant amine can be advantageously employed. Preferably, the mole ratio of reactant amine to difunctional aliphatic alcohol is in the range from about 0.1 to about 20. More preferably, the mole ratio of reactant amine to difunctional aliphatic alcohol is in the range from about 1 to about 15, even more preferably from about 1 to about 10, and most preferably from about 2 to about 10.

Although, preferably, a solvent is not used in the amination reaction, it is within the scope of the invention for a solvent to be used, if desired. Any solvent is acceptable provided that (1) it is not reactive with the difunctional alcohol and the reactant or product amines, and (2) it does not decompose under the conditions of the reaction. Some examples of suitable solvents include water, saturated aliphatic hydrocarbons such as pentane, hexane, heptane, octane, nonane, and decane, and aromatic hydrocarbons such as benzene, toluene, and xylene. The amount of solvent employed depends upon the particular reactants and reactions conditions. Any amount of solvent is acceptable that meets the intended purpose of use. If a solvent is used, the solvent typically constitutes from about 5 weight percent to about 95 weight percent of the feed stream. Preferably, the solvent constitutes from about 10 weight percent to about 80 weight percent of the feed stream.

The catalyst employed in the process of this invention is a composition containing a Group VB metal. The Group VB metals include vanadium, niobium, and tantalum. Preferably, the catalyst composition contains (a) a Group VB metal oxide, (b) a niobium phosphate or tantalum phosphate, or (c) mixtures thereof. Examples of suitable Group VB metal oxides include vanadium oxides such as $VO$, $VO_2$, $V_2O_3$, $V_2O_5$, $V_3O_5$, $V_5O_9$, $V_6O_{13}$; niobium oxides such as $NbO$, $NbO_2$, $Nb_2O_5$; tantalum oxides such as $Ta_2O_5$; as well as hydrated oxides including vanadates such as $H_3VO_4$, niobic acid such as $Nb_2O_6 \cdot xH_2O$, $H_8Nb_6O_{19} \cdot xH_2O$, and $[H_2Nb_6O_{16}]_m$, tantalic acid; Group VB metal acid salts, such as $KVO_3$, $NaVO_3$, $Na_3VO_4$, $KNbO_3$, $NaNbO_3$, $KTaO_3$, and mixtures of Group VB metal oxides, hydrated metal oxides, and/or metal acid salts. Non-stoichiometric oxides are also suitable. Preferably, the Group VB metal oxide is an oxide or hydrated oxide of niobium or tantalum. More preferably, the Group VB metal oxide is an oxide or hydrated oxide of niobium. Most preferably, the Group VB metal oxide is a hydrated niobium oxide.

Examples of suitable niobium or tantalum phosphates include $2Nb_2O_5 \cdot P_2O_5 \cdot 6H_2O$, $2Nb_2O_5 \cdot P_2O_5$, $NbOPO_4$, $PNb_9O_{25}$, $2Ta_2O_5 \cdot P_2O_5 \cdot 6H_2O$, $2Ta_2O_5 \cdot P_2O_5$, and $TaOPO_4$. Niobium or tantalum meta-phosphates, fluorophosphates, hydrated phosphates, silico-phosphates and non-stoichiometric phosphate compounds are also suitable, as are niobium or tantalum hydrogen phosphates. Preferably, the niobium or tantalum phosphate possesses a P/Nb or P/Ta mole ratio no greater than about 1.3. More preferably, the niobium or tantalum phosphate possesses a P/Nb or P/Ta mole ratio in the range from about 0.02 to about 1.0. Preferably, the phosphate is a niobium phosphate. More preferably, the phosphate is $NbOPO4$ and the hydrated forms of $NbOPO_4$.

The aforementioned examples are illustrative of the great variety of forms the catalyst can assume; however, the catalyst is not necessarily limited to only these recited examples. Other Group VB metal oxides and niobium or tantalum phosphates may be obtained which are equally suitable for the process of this invention. For example, mixtures of Group VB metal oxides, niobium phosphates, and/or tantalum phosphates can also be employed.

Generally, the common Group VB metal oxides are commercially available; while the less common oxides can be prepared by methods known in the art, such as are found in *Comprehensive Inorganic Chemistry*, Vol. 3, J. C. Bailar, Jr., H. J. Emeleus, R. Nyholm, and A. F. Trotman-Dickenson, Eds., Pergamon Press Ltd., Oxford, 1973, pp. 510–524 and 592–599.

The niobium or tantanlum phosphates are relatively easy to prepare. The preparations are also described in Comprehensive Inorganic Chemistry, ibid., pp. 612–613. Preferably, the niobium or tantalum phosphate is prepared by reacting a catalyst precursor compound containing niobium or tantalum with a phosphorus-containing compound, such as phosphoric acid, under conditions sufficient to generate the niobium or tantalum phosphate. Anhydrous or aqueous phosphoric acid can be employed, as can chlorinated or fluorinated phosphoric acids, or chlorinated or fluorinated phosphorus-containing compounds. Typical catalyst precursor compounds which can be employed as starting materials include niobium or tantalum oxides, hydrated metal oxides, halides, alkoxides, and carboxylic acid salts. Preferably, the precursor compound is a niobium or tantalum hydrated metal oxide. More specifically, the catalyst precursor is heated with phosphoric acid at about atmospheric pressure and at a temperature in the range from about 130° C. to about 200° C. The weight ratio of phosphoric acid to precursor compound is preferably in the range from about 5 to about 20, more preferably in the range from about 7 to about 15, most preferably, about 10. The phosphoric acid is typically employed as an 85 weight percent aqueous solution; however, additional water can be used to obtain phosphate catalysts having higher surface area. The heating time varies depending upon the quantity of precursor compound and the amount of water or other volatiles which are to be driven off in the heating. Typically, however, the mixture is heated for about one to two hours; however longer times may be employed. After heating, the mixture comprising a liquid phase and a solid phase is cooled. The liquid is decanted from the solid, and the solid is washed with water and filtered. The washing and filtering may be repeated several times to ensure the removal of excess acid and unwanted ions. The filtered solid is dried at a temperature in the range from about 80° C. to about 150° C. in air for a time in the range from about 2 hours to about 50 hours to yield the phosphate catalyst of the invention. Typically, the catalyst is heat treated or calcined prior to use. Preferably, the calcination is conducted at a temperature in the range from about 200° C. to about 500° C. for a time in the range from about 2 hours to about 50 hours.

Preferably, the Group VB metal oxides and niobium phosphate and tantalum phosphate compounds, described hereinbefore, are insoluble in the amination reaction mixture, thereby acting as heterogeneous catalysts. Optionally, any of the Group VB oxides or metal phosphates can be made less soluble by (a) depositing onto a support material, or (b) binding with a metal oxide or support precursor. Any support or binder material is acceptable provided that it it does not enhance the formation of undesirable cyclic products in the process of this invention. Suitable supports or binders include carbon and any refractory oxide such as alumina (hydrated and dehydrated forms), zirconia, boria, thoria, magnesia, titania, tantala, chromia, silica, kielselguhr, and mixtures of these materials. Preferably, the support or binder material is alumina, silica, or titania. More preferably, the support material or binder is an alumina or hydrated alumina, such as boehmite or pseudoboehmite alumina (aluminum oxyhydroxide). The support material typically has a surface area of at least about $0.1 \, m^2/g$. Preferably, the support material has a surface area in the range from about $5 \, m^2/g$ to about $600 \, m^2/g$, most preferably in the range from about $50 \, m^2/g$ to about $200 \, m^2/g$. These surface areas are measured by the Brunauer-Emmett-Teller (BET) method, as described by R. B. Anderson, in *Experimental Methods in Catalytic Research*, Academic Press, 1968, pp 48–66.

The Group VB metal phosphates and oxides can be applied to the support material in any known fashion, such as by impregnation or by precipitation in situ from the catalyst preparation reaction. In these preparations the phosphate or oxide is adsorbed onto the support. Alternatively, the Group VB metal oxides can be coprecipitated with the support from the corresponding alkoxides. For example, a solution of niobium ethoxide and aluminum ethoxide can be hydrolyzed to coprecipitate niobium oxide and alumina. Alternatively, the Group VB metal oxide and support can be dissolved in basic solution and coprecipitated. For example, niobic acid and alumina can be dissolved in an aqueous potassium hydroxide solution, then coprecipitated by lowering the pH. Other methods of supporting the Group VB metal oxides and phosphate catalysts are acceptable, such as is described in U.S. Pat. No. 4,337,175, incorporated herein by reference.

In a preferred method of preparation, the Group VB metal phosphate or oxide can be chemically reacted or bound onto the support. In this preparation a catalyst precursor compound, such as identified hereinbefore, is reacted with the hydroxyl functionalities of the support to yield a catalyst precursor chemically bound to the support. For example, niobium chloride reacts with the hydroxyl moieties of silica to yield niobium chloride bound through an oxygen to silicon. Typically, the niobium chloride or Group VB metal chloride is dissolved in a solvent to make a solution. Any solvent is acceptable, provided that it is not reactive with the metal chloride or the supported metal chloride. Acceptable solvents include saturated hydrocarbons, such as pentane and hexane, and aromatic hydrocarbons, such as benzene and toluene, as well as acetone, acetonitrile, chlorinated hydrocarbons, and the like. Typically, the minimum amount of solvent is used to dissolve the metal chloride. The refractory oxide is added to the resulting solution in a metal chloride/refractory oxide weight ratio in the range from about 0.0005 to about 0.60. The mixture is then rotary evaporated to remove the solvent leaving a solid of a Group VB metal chloride supported on a refractory oxide. The solid is heated at a temperature in the range from about 50° C. to about 150° C. for a time in the range from about 1 hour to about 5 hours to yield a Group VB metal chloride bound to a refractory oxide.

The bound catalyst precursor can be converted into the Group VB oxide catalyst by hydrolysis or heating. Preferably, the supported oxide catalyst is a niobium oxide supported on alumina, silica, or titania. More preferably, the supported oxide catalyst is niobium oxide supported on alumina, prepared by dehydrating a mixture of hydrated niobium oxide and boehmite or pseudoboehmite alumina. Similarly, the bound catalyst precursor can be converted into the Group VB phosphate catalyst of the invention by reaction with phosphoric acid. For example, the Group VB metal chloride bound to a refractory oxide, described hereinbefore, can be heated with an excess of 85 weight percent phosphoric acid at a temperature in the range from about 130° C. to about 200° C. for a time in the range from about 1 hour to about 5 hours to yield the niobium or tantalum phosphate supported on a refractory oxide. Preferably, the supported phosphate catalyst is niobium phosphate on alumina, silica, or titania. More preferably, the supported phosphate catalyst is niobium phosphate on silica.

The amount of catalyst which is employed in the process of this invention is any amount which is effective in producing the desired non-cyclic polyalkylenepolyamine products. The amount of catalyst varies considerably depending upon the specific reactants and reaction conditions employed. Typically, in a batch reactor the amount of catalyst is in the range from about 0.1 weight percent to about 20 weight percent based on the weight of reactant amine. Preferably, the amount of catalyst is in the range from about 1 weight percent to about 15 weight percent based on the weight of reactant amine.

The process of this invention can be carried out in any suitable reactor, including batch reactors, continuous fixed-bed reactors, slurry reactors, fluidized bed reactors, and catalytic distillation reactors. Preferably, the reactor is a continuous fixed-bed reactor.

The difunctional aliphatic alcohol and amine reactants are contacted with the catalyst at any operable temperature which promotes the amination process of this invention and yields the desired non-cyclic polyalkylenepolyamine products. Typically, the temperature is in the range from about 200° C. to about 400° C. Preferably, the temperature is in the range from about 250° C. to about 400° C. More preferably, the temperature is in the range from about 270° C. to about 320° C. Below the preferred lower temperature the conversion of difunctional alcohol may be low. Above the preferred upper temperature the selectivity for non-cyclic polyalkylenepolyamines may decrease.

Likewise, the difunctional aliphatic alcohol and amine reactants are contacted with the catalyst at any operable pressure which promotes the amination process of this invention and yields the desired non-cyclic polyalkylenepolyamine products. Typically, the pressure is sufficient to maintain the reactants in the liquid state at the temperature of the reaction. Preferably, the pressure is in the range from about atmospheric to about 4000 psig. More preferably, the pressure is in the range from about 500 psig to about 3000 psig. Most preferably, the pressure in the range from about 1000 psig to about 2000 psig. In batch reactors the pressure is autogenous, and depends on the vapor pressure of the reactants and products, and on the temperature of the reaction.

When the process of this invention is conducted in a continuous flow reactor, the flow rate of the reactants can be varied. Generally, the difunctional alcohol and the reactant amine are premixed to form a feed stream which is fed into the reactor at any operable flow rate which yields predominantly non-cyclic polyalkylenepolyamine products. The flow rate is expressed as the liquid hourly space velocity (LHSV) and is given in units of grams of total reactants per milliliter of total reactor volume per hour, $g\ ml^{-1}\ hr^{-1}$. It is preferred to employ a liquid hourly space velocity of reactants in the range from about $0.1\ g\ ml^{-1}\ hr^{-1}$ to about $10.0\ g\ ml^{-1}\ hr^{-1}$, more preferably in the range from about $0.5\ g\ ml^{-1}\ hr^{-1}$ to about $4.0\ g\ ml^{-1}\ hr^{-1}$. It should be understood that the space velocity controls the residence time of the reactants in a continuous flow reactor.

When the process of this invention is conducted in a batch reactor, the reaction time determines the length of contact between the reactants and the catalyst. Any reaction time which yields the desired non-cyclic polyalkylenepolyamine products is acceptable. The reaction time depends on the quantity of reactants, the quantity of catalyst, the temperature of the reaction and desired degree of conversion. Preferably, the reaction time in a batch reactor is in the range from about 1 hour to about 20 hours.

When the difunctional aliphatic alcohol and the reactant amine are contacted in accordance with the process of this invention, a reaction occurs to form a polyalkylenepolyamine product and water is eliminated as a by-product. If the difunctional alcohol contains two or more hydroxyl moieties, the reactant amine may react at each hydroxyl. Preferably, the product is a mixture of polyalkylenepolyamines enriched in non-cyclic products, such as straight-chain or branched chain compounds. For example, if the reactants are monoethanolamine and ethylenediamine, the polyalkylenepolyamine products are preferably diethylenetriamine and linear and branched triethylenetetramines. In addition to non-cyclic products, undesirable cyclic products containing N-heterocycles may form. Piperazine and 1,4-diaza-[2.2.2]-bicyclooctane are examples of such undesirable cyclic products.

The preferred non-cyclic polyalkylenepolyamines can be represented by the general formula:

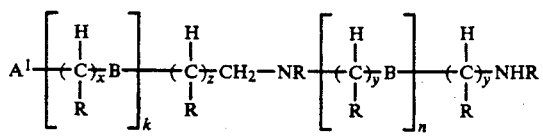

wherein each B is independently NR or O; each R is independently hydrogen, hydroxyl, amino, an alkyl moiety of $C_1$-$C_{12}$ carbon atoms, a hydroxyalkyl or aminoalkyl moiety of $C_1$-$C_{12}$ carbon atoms, or a monocyclic aromatic moiety; each x and y is independently a positive integer from 2 to about 12; z is a positive integer from 1 to about 12; k and n are each independently a positive integer from 0 to about 150; and wherein $A^1$ is OH or NHR or:

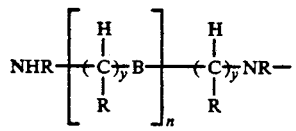

Preferably, each R is hydrogen. More preferably, each R is hydrogen, $A^1$ is $NH_2$, k is 0, y is 2, and z is 1. Most preferably, each R is hydrogen, $A^1$ is $NH_2$, k is 0, y is 2, z is 1, and n is 1, 2, or 3; thus, the polyalkylenepolyamines are diethylenetriamine, triethylenetetramine, and tetraethylenepentamine.

For the purposes of this invention, "conversion" is defined as the weight percentage of difunctional aliphatic alcohol lost as a result of reaction. The conversion can vary widely depending upon the reactants, the form of the catalyst, and the process conditions such as temperature, pressure, and flow rate. Within the preferred temperature range, as the temperature increases the conversion generally increases. Within the preferred space velocity range, as the space velocity increases the conversion generally decreases. Typically, the conversion of the difunctional alcohol is at least about 3 weight percent. Preferably, the conversion is at least about 10 weight percent, more preferably at least about 20 weight percent, even more preferably at least about 30 weight percent, and most preferably at least about 45 weight percent.

Likewise, for the purposes of this invention "selectivity" is defined as the weight percentage of total products on a feed-free basis which forms a particular polyalkylenepolyamine product. Typically, the selectivities also vary widely depending upon the reactants, the form of the catalyst, and the process conditions. Typically, the process of this invention achieves high selectivities to non-cyclic polyalkylenepolyamines. Within the preferred temperature range, as the temperature increases the selectivity for non-cyclic polyalkylenepolyamines generally decreases. Within the preferred space velocity range, as the space velocity increases the selectivity for non-cyclic polyalkylenepolyamine generally increases. Preferably, the combined selectivity to all non-cyclic polyalkylenepolyamines is at least about 50 weight percent, more preferably, at least about 60 weight percent, even more preferably at least about 75 weight percent, and most preferably at least about 85 weight percent.

Where applicable, the efficiency of the amination reaction in forming non-cyclic polyalkylenepolyamines is measured by the weight ratio of diethylenetriamine to piperazine, abbreviated DETA/PIP. The higher the value of this ratio, the more non-cyclic polyalkylenepolyamines are present in the product mixture. Preferably, the DETA/PIP weight ratio is at least about 3. More preferably, the DETA/PIP weight ratio is at least about 10; most preferably, at least about 20. Another measure of the efficiency of forming non-cyclic products is the weight percentage of triethylenetetramines which are non-cyclic, % NC TETA. Preferably, % NC TETA is at least about 50 weight percent. More preferably, % NC TETA is at least about 75 weight percent; most preferably, at least about 90 weight percent.

Illustrative Embodiments

The following examples illustrate the invention, but are not intended to be limiting thereof. All percentages are given as weight percent, unless noted otherwise. In some instances the following abbreviations are used to indicate the reactants and products:

| | |
|---|---|
| MEA | monoethanolamine |
| EDA | ethylenediamine |
| AEEA | N-(2-aminoethyl)ethanolamine |
| DETA | diethylenetriamine |
| TETA | triethylenetetramine |
| TEPA | tetraethylenepentamine |
| PIP | piperazine |
| AEP | N-(2-aminoethyl)piperazine |
| DABCO | 1,4-diaza-[2.2.2]-bicyclooctane |

Example 1

(a) Preparation of Niobium Phosphate Catalyst

A mixture is prepared containing niobic acid, $Nb_2O_5 \cdot xH_2O$, (60.33 g; 0.211 moles; Niobium Products Company, AD-460) and 85% phosphoric acid (602.20 g; 5.22 moles). The mixture is heated to 150° C. with stirring. The niobium oxide dissolves to form a pink solution, and upon heating a precipitate forms. The precipitate is boiled in the phosphoric acid for about 2 hours. The boiled mixture is cooled to room temperature, and the liquid phase is decanted from the precipitate. The precipitate is washed by stirring with 500 ml of water, after which the aqueous mixture is filtered. The washing and filtering cycle is repeated five times. The filtered solid is dried at 110° C. under air for 2½ days to yield a catalyst of niobium phosphate. The elemental analysis and X-ray diffraction pattern of the catalyst are consistent with the composition $NbOPO_4$. The P/Nb mole ratio, as determined by neutron activation analysis and X-ray fluorescence, is 1.03.

(b) Amination in Batch Reactor

A mixture (50 g) of ethylenediamine and monoethanolamine in an EDA/MEA mole ratio of 2/1 is loaded into a 300 ml autoclave with the niobium phosphate catalyst (2.0 g), prepared hereinabove. The autoclave is sealed and purged with nitrogen gas three times. The temperature of the autoclave is raised to 265° C. and held thereat for a total of 600 minutes. The cooled reaction products are analyzed by gas-phase chromatography. A CAM (Carbowax amine deactivated) capillary column (30 m×0.25 mm dia.) is employed for the analysis of total amines. Isomer distributions are determined on an SE-54 capillary column (30 m×0.25 mm dia.). A DB-5 (15 m×0.25 mm dia.) column is also used for analyzing products and isomers. The conversion of MEA is 60 percent and the selectivities, based on a feed-free and water-free basis, are the following: DETA, 84.1 percent; TETA, 7.1 percent; AEEA, 5.5 percent; PIP, 1.9 percent; and AEP, 1.4 percent. The DETA/PIP weight ratio is 44.2 and the percentage of non-cyclic TETA's (% NC TEIA) is 94.7 percent. The data show that monoethanolamine is aminated with ethylenediamine in the presence of an unsupported niobium phosphate catalyst to a mixture of polyethylenepolyamines which are predominantly non-cyclic.

(c) Amination in Continuous Flow Reactor

The niobium phosphate catalyst (10 g), prepared hereinabove, is loaded into a stainless steel, tubular, fixed-bed continuous flow reactor (approximately 6 inches long × 0.5 inch diameter). A feedstream comprising monoethanolamine and ethylenediamine in an EDA/MEA mole ratio of 2/1 is fed upward through the catalyst for several days at a variety of temperatures, pressures, and flow rates. The process conditions and results are presented in Table I.

crushed and sieved to 14–20 mesh prior to use in the reactor. The sieved niobic acid (23 g) is loaded into the tubular, fixed-bed reactor of Example 1(c). A feedstream comprising N-(2-aminoethyl)ethanolamine and diethylenetriamine in a DETA/AEEA mole ratio of 3/1 is passed upward through the catalyst bed at a flow rate of about 1.3 g ml$^{-1}$ hr$^{-1}$ The process conditions and results are presented in Table II.

TABLE II[1]

| Ex. 2 | T (°C.) | P psig | % AEEA Conversion | % Selectivity (DETA-AEEA free and H$_2$O-free basis)[2] | | | | | |
|---|---|---|---|---|---|---|---|---|---|
| | | | | EDA | PIP | AEP | TETA | TEPA (% NC TEPA)[3] | Others[4] |
| a | 291 | 1400 | 99.2 | 9.2 | 12.6 | 8.1 | 24.8 | 41.5 (84.0) | 3.8 |
| b | 265 | 1400 | 77.6 | 4.2 | 10.4 | 3.5 | 14.7 | 59.4 (96.8) | 7.8 |
| c | 260 | 1400 | 66.2 | 4.1 | 11.7 | 3.1 | 11.9 | 65.0 (98.7) | 4.2 |

[1]Feedstream comprises N-(2-aminoethyl)ethanolamine and diethylenetriamine in a DETA/AEEA mole ratio of 3/1. Catalyst (23 g) is niobic acid.
[2]Selectivities are calculated on a DETA, AEEA, and H$_2$O free basis from gc area percentages corrected for individual response factors.
[3]% NC TEPA is the percentage of tetraethylenepentamines which are non-cyclic.
[4]Others include higher homologues of ethyleneamines.

The data show that N-(2-aminoethyl)ethanolamine is aminated by diethylenetriamine in the presence of a niobic acid catalyst to predominantly non-cyclic polyethylenepolyamines.

Example 3

(a) Preparation of Boehmite-Supported Niobic Acid Catalyst

Boehmite or pseudoboehmite (60.0 g; Davison Alpha Alumina Monohydrate) and niobic acid, Nb$_2$O$_5$.xH$_2$O (60.0 g; Niobium Products Corp., CBMM number AD460) are mixed together, and the mixture is pressed at 20,000 psi into cylindrical pellets 1 inch in diameter by 1 inch in height. Each pellet contains approximately

TABLE I[1]

| Exp. 1(c) | Temp. °C. | Pres. psig | LHSV g ml$^{-1}$ hr$^{-1}$ | % MEA Conversion | % Selectivity (EDA-MEA free and H$_2$O-free basis)[2] | | | | | | |
|---|---|---|---|---|---|---|---|---|---|---|---|
| | | | | | DETA | TETA (% NC TETA)[3] | TEPA | PIP | AEP | AEEA | DETA/PIP |
| (1) | 255 | 1428 | 0.54 | 22.9 | 83.6 | 8.43 (98.5) | 0.83 | 1.33 | 1.86 | 4.00 | 62.8 |
| (2) | 274 | 1434 | 1.38 | 35.9 | 77.8 | 10.7 (97.2) | 2.80 | 1.60 | 1.47 | 5.70 | 48.6 |
| (3) | 275 | 1428 | 0.97 | 43.0 | 74.3 | 12.8 (97.6) | 2.71 | 2.09 | 1.89 | 6.19 | 35.6 |
| (4) | 291 | 1428 | 0.55 | 78.3 | 53.8 | 21.0 (86.6) | 9.74 | 6.73 | 6.25 | 2.53 | 8.0 |

[1]Feedstream comprises monoethanolamine and ethylenediamine in an EDA/MEA mole ratio of 2/1. Catalyst (10 g) is NbOPO$_4$.
[2]Selectivities are calculated on an EDA, MEA, and H$_2$O free basis from gc area percentages corrected for individual response factors.
[3]% NC TETA is the weight percentage of triethylenetetramines which are non-cyclic.

It is seen that niobium phosphate catalyzes the amination of monoethanolamine by ethylenediamine to predominantly non-cyclic polyethylenepolyamines, including diethylenetriamine and triethylenetetramines.

Example 2 Amination of N-(2-aminoethyl)ethanolamine

Niobic acid (Nb$_2$O$_5$.xH$_2$O; Niobium Products Corp., CBMM number AD222) is pressed at a pressure of 20,000 psi into cylindrical pellets 1 inch in diameter by 1 inch in height. Each pellet contains approximately 25 grams of niobic acid. The pressed pellets are dried at 120° C. for 4 hours, then heated slowly to 300° C. and calcined thereat overnight. The calcined pellets are 20 grams of material. The pressed pellets are dried at 120° C. for 5 hours, then heated slowly to a temperature of 400° C. and calcined thereat overnight to yield a boehmite-supported niobic acid catalyst. The calcined catalyst pellets are crushed and sieved to 14–20 mesh prior to use in the reactor.

(b) Amination of Monoethanolamine

The boehmite-supported niobic acid catalyst (20 g), prepared hereinabove, is loaded into the tubular, fixed-bed reactor of Example 1(c). A feedstream comprising monoethanolamine and ethylenediamine in an EDA/-

MEA mole ratio of 2/1 is passed upward through the catalyst bed at a variety of process conditions with the results shown in Table III.

times. The washed material is dried at 120° C. overnight, then calcined at 300° C. overnight to yield a niobium phosphate catalyst.

TABLE III[1]

| Ex. 3 | T °C. | P psig | LHSV g ml$^{-1}$ hr$^{-1}$ | % MEA Conversion | % Selectivity (MEA-EDA free and H$_2$O-free basis)[2] | | | | | | |
|---|---|---|---|---|---|---|---|---|---|---|---|
| | | | | | PIP | DETA | AEEA | AEP | TETA (% NC TETA)[3] | TEPA | DETA PIP |
| a | 290 | 1383 | 0.95 | 57.54 | 4.53 | 65.69 | 3.63 | 3.01 | 19.3 (95.1) | 3.85 | 14.5 |
| b | 290 | 1379 | 1.24 | 33.53 | 5.67 | 76.81 | 5.14 | 1.88 | 10.50 (100) | 0 | 13.5 |
| c | 290 | 1370 | 1.48 | 24.81 | 3.41 | 83.86 | 5.97 | 1.06 | 5.70 (100) | 0 | 24.6 |
| d | 290 | 1381 | 0.98 | 56.60 | 4.54 | 65.13 | 4.38 | 3.10 | 19.91 (95.8) | 2.95 | 14.4 |

[1]Feedstream comprises monoethanolamine and ethylenediamine in an EDA/MEA mole ratio of 2/1. Catalyst (20 g) is boehmite-supported niobic acid.
[2]Selectivities calculated on an MEA, EDA, H$_2$O free basis from gc area percentages corrected for individual response factors.
[3]% NC TETA is the weight percentage of triethylenetetramines which are non-cyclic.

It is seen that monoethanolamine is aminated by ethylenediamine in the presence of a boehmite-supported niobium oxide catalyst to predominantly non-cyclic polyethylenepolyamines.

Examples 4 (a–g)

Preparation of Niobium Phosphate Catalysts Catalysts 4(a–d)

A series of four niobium phosphate catalysts having P/Nb mole ratios less than 1.35 is prepared generally as follows:

A predetermined amount of 85 weight percent phosphoric acid is diluted with water to a total of 30 ml volume. The aqueous phosphoric acid solution (30 ml) is poured over niobic acid (10 g; Nb$_2$O$_5$.xH$_2$O; Niobium Products Corp., CBMM number AD222), and the mixture is stirred at room temperature (about 23° C.) for 1 hour. After stirring, the mixture is dried under air at room temperature overnight. The mixture is further dried at 130° C. for 4 hours, and then dried at 300° C. overnight to yield a niobium phosphate catalyst. Details of the preparations and the P/Nb mole ratios are given in Table IV.

Catalyst 4(e)

Niobic acid, Nb$_2$O$_5$.xH$_2$O (10 g; Niobium Products Corp., CBMM number AD222), is heated at 185° C. for 2 hours in 100 g of 85 weight percent phosphoric acid. After cooling to room temperature, the material is stirred with 100 ml of water. The aqueous mixture is filtered, then washed with 200 ml of water and filtered times more. The washed material is dried at 130° C. for 4 hours and then dried overnight at 300° C. to yield a niobium phosphate catalyst.

Catalyst 4(f)

Niobic acid powder, Nb$_2$O$_5$.xH$_2$O (120 g; Niobium Products Corp., CBMM number AD460) and phosphoric acid (1200 g; 85 weight percent) are stirred and heated to boiling. At 145° C. the niobic acid dissolves. The solution is heated further, and at 154° C. a solid precipitates. Upon further heating and at about 165° C. the mixture forms a paste or thick slurry. The slurry is heated at 165° C. for 1 hour and then cooled to room temperature overnight. To the cooled mixture is added 500 cc of water. The aqueous mixture is filtered, then washed with 500 cc of water and filtered three more times. The washed material is dried at 120° C. overnight, then calcined at 300° C. overnight to yield a niobium phosphate catalyst.

The catalysts 4(a–f) are analyzed by neutron activation analysis and X-ray fluorescence to determine the P/Nb mole ratio. It is found that the P/Nb mole ratios vary from 0.28 to 1.35, as shown in Table IV.

(g) Amination of Monoethanolamine

Each of the niobium phosphate catalysts 4(a–f), prepared hereinabove, is tested in the amination of monoethanolamine by ethylenediamine according to the following general procedure:

A mixture (45.0 g) comprising monoethanolamine and ethylenediamine in an EDA/MEA mole ratio of 2/1 is loaded into a 300 ml Parr pressure reactor equipped with mechanical agitation. The niobium phosphate catalyst (1 g) to be tested is added to the reactor, and the reactor is sealed. The sealed reactor is flushed three times with nitrogen gas. After flushing, the temperature of the reactor is raised to 290° C. over a period of 1 hour. The reaction mixture is held with stirring at 290° C. for either 300 minutes or 600 minutes. The reaction mixture is then cooled to room temperature. Samples of the used catalysts at 300 minutes and 600 minutes are analyzed by neutron activation analysis and X-ray flourescence with the results shown in Table IV.

TABLE IV

| Ex. 4 | H$_3$PO$_4$[1] g | P/Nb Mole Ratio[2] | | | | P Conc. ppm (Residue 600 min)[3] |
|---|---|---|---|---|---|---|
| | | Fresh | Used 300 min | Used 600 min | Residue[3] 600 min | |
| a | 1.96 | 0.28 | 0.24 | 0.27 | N.O. | N.O. |
| b | 3.94 | 0.55 | 0.54 | 0.62 | N.O. | N.O. |
| c | 5.91 | 0.78 | 0.85 | 0.75 | 2.53 | 160 |
| d | 7.88 | 0.76 | 1.05 | 0.88 | N.O. | N.O. |
| e | — | 1.35 | 1.27 | 1.24 | N.O. | N.O. |
| f | — | 1.25 | 1.15 | 1.24 | N.O. | N.O. |

[1]85 wt. % phosphoric acid, as indicated, diluted to 30 ml total volume with H$_2$O, poured over niobic acid (10 g), stirred, and dried to yield niobium phosphate catalyst. Refer to test for preparation of 4e and 4f.
[2]P/Nb mole ratio of niobium phosphate catalyst, fresh and used, determined by X-ray fluorescence. P/Nb mole ratio of residue determined by neutron activation analysis.
[3]Residue is a wet, white solid other than catalyst recovered from amination reaction. N.O. means no residue is observed. No residue is observed in any sample at 300 minutes.

It is seen that the fresh niobium phosphate catalysts prepared hereinabove have a P/Nb mole ratio in the range from about 0.28 to about 1.35. It is further seen that the P/Nb mole ratio in the used catalysts is close to the mole ratio of the fresh catalysts. This result indicates that the niobium phosphate catalysts substantially maintain their compositional integrity throughout the amination reaction. With the exception of catalyst 4(c), all examples 4(a, b, d–f) show no residue at either 300 minutes or 600 minutes. In one sample (4c) a white, fluffy residue is separated wet from the catalyst at 600 minutes, and found to have a P/Nb mole ratio of 2.53. This residue indicates that some decomposition of catalyst 4(c) occurs producing a material which is significantly enriched in phosphorus.

In addition to the analysis of the used catalysts, an analysis of the products of the amination reaction is conducted by gas phase chromatography on an SE 54 capillary column, as described in Example 1(b) hereinbefore. The products for each run are found to be predominantly non-cyclic polyethylenepolyamines, including diethylenetriamine and linear and branched triethylenetetramines, as shown in Table V for Examples 4(a) and 4(f).

Comparative Material CE 1(b)

Pyrophosphoric acid, $H_4P_2O_7$ (210 g), is melted at about 70° C. and poured over niobic acid (19.4 g). The resulting mixture is heated to a temperature of 210° C. whereupon the niobic acid dissolves. Heating is continued to 230° C. whereupon a precipitate forms. Heating is continued further until a temperature of 270° C. is obtained, and the temperature is held thereat for 15 minutes. The heated mixture is cooled to room temperature. The cooled mixture is washed with 200 ml of water and filtered. The washed material is dried at 150° C. for 1 hour and at 300° C. overnight to yield a niobium pyrophosphate having a P/Nb mole ratio of 1.74.

Comparative Materials CE 1(c)

Phosphoric acid (15.76 g; 85 wt. %) is diluted to 30 ml total volume with water. The aqueous phosphoric acid solution is poured over niobic acid (10.0 g; Nio-

TABLE V[1]

| Exp. | % MEA Conversion | % Selectivity (EDA-MEA free and H2O-free basis)[2] | | | | | | |
|---|---|---|---|---|---|---|---|---|
| | | DETA | TETA (% NC TETA)[3] | TEPA | PIP | AEP | AEEA | DETA/PIP |
| 4(a) | 54.6 | 63.3 | 16.1 (88.5) | 6.56 | 3.70 | 4.13 | 6.23 | 17.1 |
| 4(f) | 51.6 | 63.4 | 16.8 (93.5) | 8.26 | 3.17 | 2.35 | 5.98 | 20.0 |
| CE 1(c) | 46.7 | 68.4 | 12.4 (92.2) | 1.34 | 12.80 | 3.61 | 1.40 | 5.36 |

[1]Feedstream comprises monoethanolamine and ethylenediamine in an EDA/MEA mole ratio of 2/1.
[2]Selectivities are calculated on an EDA, MEA, and H2O free basis from gc area percentages corrected for individual response factors.
[3]% NC TETA is the weight percentage of triethylenetetramines which are non-cyclic.

Comparative Experiment 1

A series of four niobium phosphate materials with P/Nb mole ratios greater than 1.35 is prepared as described hereinbelow. The comparative materials CE 1(a–d) are analyzed by neutron activation analysis and X-ray fluorescence to determine their P/Nb mole ratio, which is given in Table VI.

Comparative Material CE 1(a)

Phosphoric acid (11.82 g; 85 wt. %) is diluted to 30 ml total volume with water. The aqueous phosphoric acid solution is poured over niobic acid (10.0 g; Niobium Products Corp., CBMM number AD222), and the mixture is stirred and dried according to the general procedure of Examples 4(a–d) to yield a niobium phosphate having a P/Nb mole ratio of 1.41.

bium Products Corp., CBMM number AD222), and the mixture is stirred and dried according to the general procedure of Examples 4(a–d) to yield a niobium phosphate having a P/Nb mole ratio of 2.22.

Comparative Material CE 1(d)

A niobium phosphate having a P/Nb mole ratio of 3.74 is prepared as in Comparative Experiment CE 1(c) hereinabove, except that the amount of 85 weight percent phosphoric acid is 23.64 g.

(e) Amination of Monoethanolamine

Each of the niobium phosphate comparative materials CE 1(a–d), prepared hereinabove, is tested in the amination of monoethanolamine by ethylenediamine according to the general procedure of Example 4(g). Samples of the used comparative materials at 300 minutes and 600 minutes are analyzed by neutron activation analysis and X-ray fluorescence, as shown in Table VI.

TABLE VI

| CE 1 | $H_3PO_4$[1] g | P/Nb Mole Ratio[2] | | | | | P Conc. (Residue 600 min)[3] ppm |
|---|---|---|---|---|---|---|---|
| | | Fresh | Used[4] 300 min | Residue[3,4] 300 min | Used 600 min | Residue[3] 600 min | |
| a | 11.82 | 1.41 | 1.30 | 2.45 | 1.14 | 4.32 | 950 |
| b | — | 1.74 | N.M. | N.M. | 1.75 | 3.39 | 2600 |
| c | 15.76 | 2.22 | N.M. | N.M. | 2.29 | 4.27 | 9100 |

TABLE VI-continued

| CE 1 | $H_3PO_4$[1] g | P/Nb Mole Ratio[2] | | | | P Conc. (Residue 600 min)[3] ppm |
|---|---|---|---|---|---|---|
| | | Fresh | Used[4] 300 min | Residue[3,4] 300 min | Used 600 min | Residue[3] 600 min | |
| d | 23.64 | 3.74 | N.M. | N.M. | 2.57 | 7.47 | 12,200 |

[1] 85 wt. % phosphoric acid, as indicated, diluted to 30 ml total volume with $H_2O$, poured over niobic acid (10 g), stirred, and dried to yield niobium phosphate catalyst. Refer to text for preparation of CE 1(b).
[2] P/Nb mole ratio of niobium phosphate catalyst, fresh and used, determined by X-ray fluorescence. P/Nb mole ratio of residue determined by neutron activation analysis.
[3] Residue refers to white, wet solid other than catalyst recovered from amination reaction.
[4] N.M. means not measured.

It is seen that the used comparative materials CE 1(a) and CE 1(d) exhibit a substantially lower P/Nb mole ratio than the corresponding fresh materials. In addition, in each comparative example a white, wet residue is obtained which has a P/Nb mole ratio at least double the ratio of the fresh catalyst. This residue is a material which comes from the catalyst and which is enriched in phosphorus content. The concentration of phosphorus in this material is observed to increase significantly as the P/Nb mole ratio of the fresh catalyst increases. It is concluded that the comparative materials are disintegrating in the amination reaction.

When the concentration of phosphorus in the residues (600 minutes) of the Comparative Experiments is compared with the residue (600 minutes) of Example 4(c), it is seen that the residues of the Comparative Experiments exhibit at least about a 6 to about 76 times greater phosphorus concentration than the residue of Example 4(c). Moreover, when Comparative Experiments CE 1(a-d) are compared with Examples 4(a-f) it is seen that fresh catalysts having a P/Nb mole ratio less than about 1.35 retain their physical integrity in the amination reaction for a longer period of time than do fresh comparative materials having a P/Nb mole ratio greater than about 1.4.

In addition to the analyses described hereinabove, the products of the amination reaction are analyzed by gas phase chromatography for each comparative experiment. The reaction products are found to be predominantly non-cyclic polyethylenepolyamines, including diethylenetriamine and linear and branched triethylenetetramines. However, when Comparative Experiment CE 1(c) is compared with Examples 4(a) and 4(f) as shown in Table V (DETA/PIP ratio), it is observed that the weight ratio of non-cyclic to cyclic products of the comparative material (P/Nb mole ratio, 2.22) is significantly lower than the weight ratio of non-cyclic to cyclic products of the Examples (P/Nb mole ratio, 0.28 and 1.25).

We claim:

1. A process for preparing non-cyclic polyalkylenepolyamines comprising contacting a difunctional aliphatic alcohol and a reactant amine in the presence of a catalyst under reaction conditions such that a mixture of polyalkylenepolyamines enriched in non-cyclic products is formed, the catalyst containing (a) a niobium phosphate or tantalum phosphate wherein the mole ratio f phosphorus to niobium or tantalum is no greater than about 1.3 or mixtures thereof, or (b) mixtures of said niobium and/or tantalum phosphates with a Group VB metal oxide.

2. The process of claim 1 wherein the difunctional aliphatic alcohol is represented by the formula:

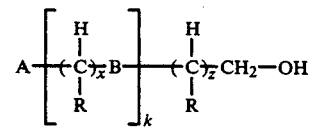

wherein A is OH or NHR; each B is in independently NR or O; each R is independently hydrogen, hydroxyl, amino, an alkyl moiety of $C_1-C_{12}$ carbon atoms, a hydroxyalkyl or aminoalkyl moiety of $C_1-C_{12}$ carbon atoms, or a monocyclic aromatic moiety; x is a positive integer from 2 to about 12; k is a positive integer from 0 to about 150; and z is an integer from 0 to about 12.

3. The process of claim 2 wherein each R is hydrogen.

4. The process of claim 3 wherein x is 2 and z is 1.

5. The process of claim 4 wherein each R is hydrogen, A is $NH_2$, k is 0, z is 1, and the difunctional aliphatic alcohol is monoethanolamine.

6. The process of claim 1 wherein the reactant amine is an alkylenepolyamine represented by the formula:

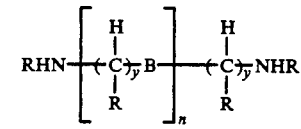

wherein each B is independently NR or O; each R is independently hydrogen, hydroxyl, amino, an alkyl moiety of $C_1-C_{12}$ carbon atoms, a hydroxyalkyl or aminoalkyl moiety of $C_1-C_{12}$ carbon atoms, or a monocyclic aromatic moiety; each y is independently a positive integer from 2 to about 12; and n is a positive integer from 0 to about 150.

7. The process of claim 6 wherein each B is NR and each R is hydrogen.

8. The process of claim 7 wherein each B is NR, each R is hydrogen, each y is 2 and the alkylenepolyamine is an ethylenepolyamine.

9. The process of claim 8 wherein the alkylenepolyamine is ethylenediamine.

10. The process of claim 1 wherein the mole ratio of reactant amine to difunctional aliphatic alcohol is in the range from about 0.1 to about 20.

11. The process of claim 1 wherein the phosphorus to niobium mole ratio is in the range from about 0.02 to about 1.0.

12. The process of claim 1 wherein the Group VB metal oxide is a niobium oxide.

13. The process of claim 12 wherein the niobium oxide is niobic acid.

14. The process of claim 13 wherein the niobic acid is supported on boehmite alumina.

15. The process of claim 1 wherein the catalyst contains a niobium phosphate.

16. The process of claim 15 wherein the niobium phosphate is NbOPO4 or hydrated NbOPO4.

17. The process of claim 1 wherein the temperature is in the range from about 200° C. to about 400° C.

18. The process of claim 1 wherein the pressure is in the range from about atmospheric to about 4000 psig.

19. The process of claim 1 wherein the liquid hourly space velocity is in the range from about 0.1 g ml$^{-1}$ hr$^{-1}$ to about 10.0 g ml$^{-1}$ hr$^{-1}$.

20. The process of claim 1 wherein the non-cyclic polyalkylenepolyamine is represented by the formula:

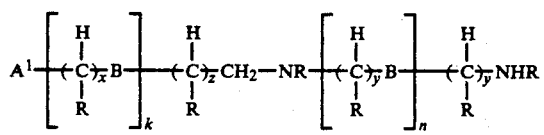

wherein each B is independently NR or O; each R is independently hydrogen, hydroxyl, amino, an alkyl moiety of $C_1$-$C_{12}$ carbon atoms, a hydroxyalkyl or aminoalkyl moiety of $C_1$-$C_{12}$ carbon atoms, or a monocyclic aromatic moiety; x and y are each independently positive integers from 2 to about 12; z is a positive integer from 0 to about 12; k and n are each independently positive integers from 0 to about 150; and wherein $A^1$ is NHR or:

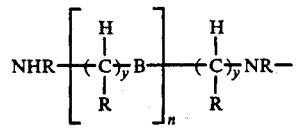

21. The process of claim 20 wherein each R is hydrogen, $A^1$ is $NH_2$, k is 0, y is 2, z is 1, and n is 1, 2, or 3.

22. A process of preparing predominantly non-cyclic polyethylenepolyamines comprising contacting monoethanolamine with ethylenediamine in the presence of a catalyst containing (a) niobium phosphate wherein the phosphorus to niobium mole ratio is no greater than about 1.3 or (b) mixtures thereof with niobium oxide, under conditions such that non-cyclic polyethylenepolyamines are formed in a selectivity of at least about 50 weight percent.

23. The process of claim 22 wherein the diethylenetriamine to piperazine weight ratio is at least about 3.

24. The process of claim 22 wherein the weight percentage of non-cyclic triethylenetetramines is at least about 80 percent.

25. The process of claim 22 wherein the diethylenetriamine to piperazine weight ratio is at least about 10.

26. The process of claim 22 wherein the weight percentage of non-cyclic triethylenetriamines is at least about 90 weight percent.

* * * * *

UNITED STATES PATENT AND TRADEMARK OFFICE
CERTIFICATE OF CORRECTION

PATENT NO. : 5,011,999
DATED : April 30, 1991
INVENTOR(S) : Robert G. Bowman, George E. Hartwell, and David C. Molzahn It is certified that error appears in the above-identified patent and that said Letters Patent is hereby corrected as shown below:

On the title page, under Inventors, please delete the following names from the list " Enrique G. Ramirez and John E. Lastovica, Jr. ". The correct inventors names are -- Robert G. Bowman, George E. Hartwell, and David C. Molzahn --.

Signed and Sealed this

Twelfth Day of January, 1993

Attest:

DOUGLAS B. COMER

*Attesting Officer*     Acting Commissioner of Patents and Trademarks